United States Patent
Scagliarini

(12) 
(10) Patent No.: US 6,536,278 B1
(45) Date of Patent: Mar. 25, 2003

(54) TRANSDUCER PROTECTION DEVICE, PARTICULARLY FOR HEMODIALYSIS PROCESSES

(75) Inventor: Massimo Scagliarini, Bologna (IT)

(73) Assignee: GVS S.r.l., Zola Predosa (IT)

( * ) Notice: Subject to any disclaimer, the term of this patent is extended or adjusted under 35 U.S.C. 154(b) by 0 days.

(21) Appl. No.: 09/566,077

(22) Filed: May 8, 2000

(30) Foreign Application Priority Data

Nov. 8, 1999 (IT) .......................................... B099A0602

(51) Int. Cl.$^7$ .............................................. G01L 19/14
(52) U.S. Cl. ............................ 73/431; 73/706; 600/488
(58) Field of Search .................... 73/706, 431; 600/488

(56) References Cited

U.S. PATENT DOCUMENTS

| | | | | |
|---|---|---|---|---|
| 4,314,480 A | * | 2/1982 | Becker ......................... | 73/706 |
| 4,461,181 A | * | 7/1984 | North, Jr. ..................... | 73/49 |
| 4,631,685 A | * | 12/1986 | Peter ........................... | 364/476 |
| 4,679,421 A | * | 7/1987 | Barree .......................... | 73/38 |
| 4,727,753 A | * | 3/1988 | Baumann et al. ............ | 73/706 |
| 4,822,339 A | * | 4/1989 | Tran ............................. | 604/82 |
| 4,881,320 A | * | 11/1989 | Kohle et al. .................. | 29/841 |
| 5,019,723 A | * | 5/1991 | Tran ............................. | 307/400 |
| 5,217,222 A | * | 6/1993 | Rudell et al. ................. | 273/67 R |
| 5,234,369 A | * | 8/1993 | Forbes et al. ................ | 446/207 |
| 5,410,916 A | * | 5/1995 | Cook ........................... | 73/706 |
| 5,749,726 A | * | 5/1998 | Kinsel .......................... | 433/80 |
| 5,932,175 A | * | 8/1999 | Knute et al. ................. | 422/82.01 |
| 6,171,253 B1 | * | 1/2001 | Bullister et al. ............. | 600/486 |

FOREIGN PATENT DOCUMENTS

| | | |
|---|---|---|
| EP | 0 652 018 | 5/1995 |
| EP | 0 878 628 | 11/1998 |
| EP | 0 887 085 | 12/1998 |

* cited by examiner

*Primary Examiner*—Hezron Williams
*Assistant Examiner*—Charles D. Garber
(74) *Attorney, Agent, or Firm*—Guido Modiano; Albert Josif; Daniel O'Byrne

(57) ABSTRACT

A transducer protection device, particularly for hemodialysis processes, which comprises a first element and a second element made of plastics which are coupled coaxially with respect to a common axis and respectively comprise a first tubular connector and a second tubular connector which are blended with respective flanges which are coaxial to the common axis; the flanges are coupled to each other along their peripheral region by ultrasonic thermal bonding; the device has a recess formed frontally on a first one of the flanges, the recess being coaxial to the common axis and being suitable for accommodating, in a fixed arrangement, a semipermeable membrane by imbibition of melted plastics along a circular border region by the thermal bonding provided on a circular ridge which is shaped complementarily to the border region and protrudes frontally from the second flange so as to achieve bonding between the first and second flanges and the membrane.

9 Claims, 4 Drawing Sheets

TRANSDUCER PROTECTION DEVICE, PARTICULARLY FOR HEMODIALYSIS PROCESSES

BACKGROUND OF THE INVENTION

The present invention relates to a transducer protection device, particularly for hemodialysis processes, suitable for measuring the blood pressure in the patient during hemodialysis.

It is known that in this field one of the strongly felt problems is to prevent the blood pressure measurement device from becoming infected by any virus present in a patient which may be transmitted to a subsequent patient, to operators and even to the entire hemodialysis machine.

In particular, it has been found that the protective devices currently in use consist of elements which, through ducts, are connected at one end to a main duct, which connects the patient to the hemodialysis machine, and at the other end to another duct which leads to a blood pressure measurement device. Said elements comprise two tubular connectors made of plastics being connected to the ducts. The two tubular connectors blend with two respective circular flanges between which, during sealing, a membrane of semipermeable material is interposed, which is suitable for retaining the liquids and/or the viruses present in said liquids. The membrane covers the entire circular surface of the two flanges and is fixed thereon during the sealing/gluing of the flanges.

Although this solution solves the problem of protection from viral infections, it requires considerably complex operations for construction, with consequent damage risks to the membrane, and moreover it does not ensure the necessary tightness of the membrane between the flanges.

SUMMARY OF THE INVENTION

The aim of the present invention is to obviate said drawbacks by providing a transducer protection device which allows excellent membrane tightness.

Within the scope of this aim, an object of the present invention is to ensure protection against viral particles for the pressure measurement device and for the hemodialysis machine, as well as for the patient and the health operators.

Another object of the present invention is to provide a structure which is simple, relatively easy to be manufactured, safe in use, effective in operation and has a relatively low cost.

These and other objects are achieved by the present transducer protection device, particularly for hemodialysis processes, which comprises a first element and a second element made of plastics which are mutually coupled coaxially with respect to a common axis and respectively comprise a first tubular connector and a second tubular connector blended with respective flanges which are coaxial to said common axis, said flanges being coupled to each other along their peripheral region by ultrasonic thermal bonding, said device being characterized in that a recess is formed frontally on a first one of said flanges, said recess being coaxial to said common axis and being suitable to accommodate, in a fixed arrangement, a semipermeable membrane by imbibition of melted plastics along a circular border region by way of the thermal bonding provided on a circular ridge which is shaped complementarily to said border region and protrudes frontally from the second flange so as to achieve bonding between said first and second flanges and said membrane.

BRIEF DESCRIPTION OF THE DRAWINGS

Further particularities will become better apparent from the detailed description of a preferred but not exclusive embodiment of a transducer protection device, particularly for hemodialysis processes, according to the invention, illustrated only by way of non-limitative example in the accompanying drawings, wherein.

DESCRIPTION OF THE PREFERRED EMBODIMENTS

Figure 1:
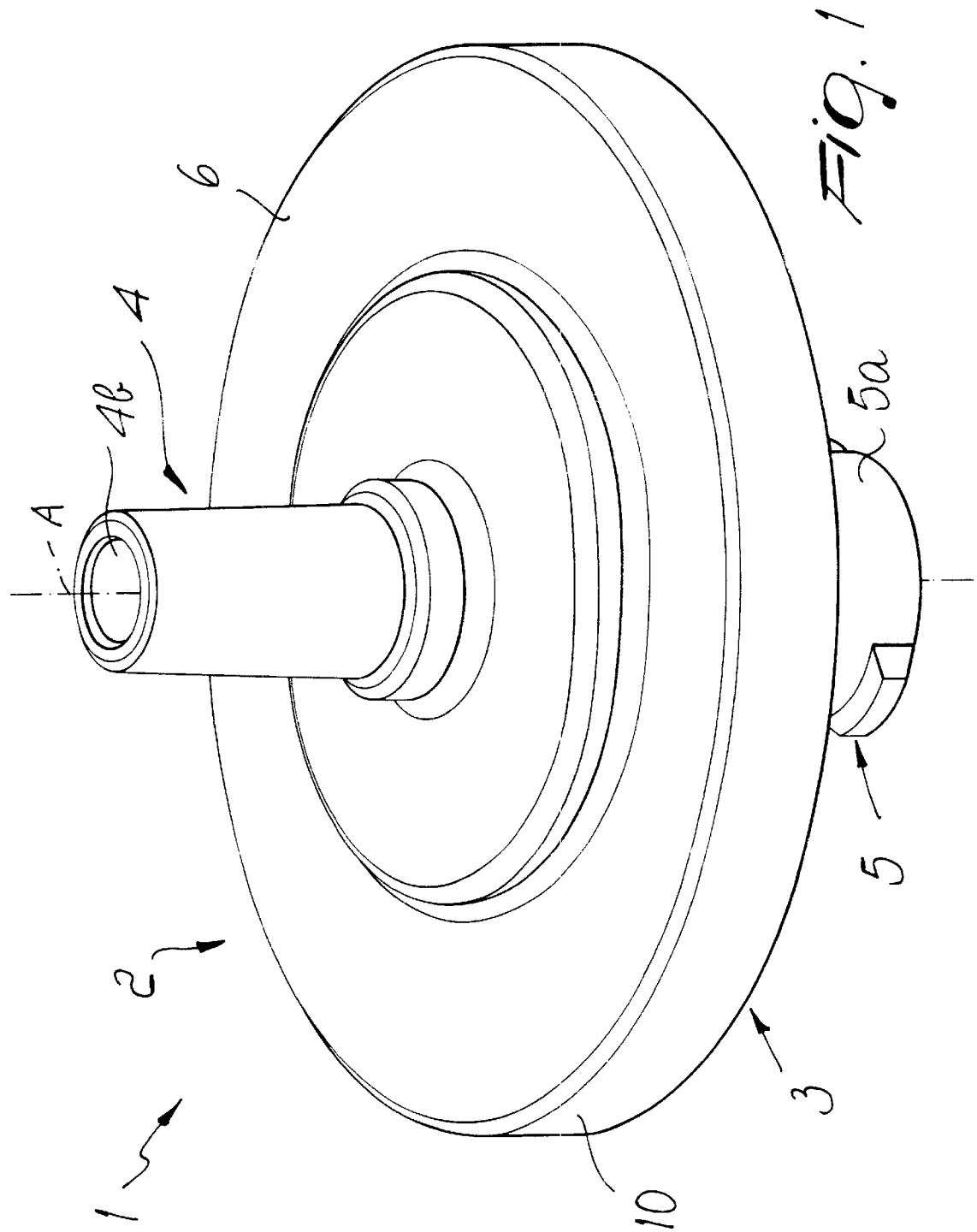
FIG. 1 is a perspective view of the device according to the invention.
Figure 2:
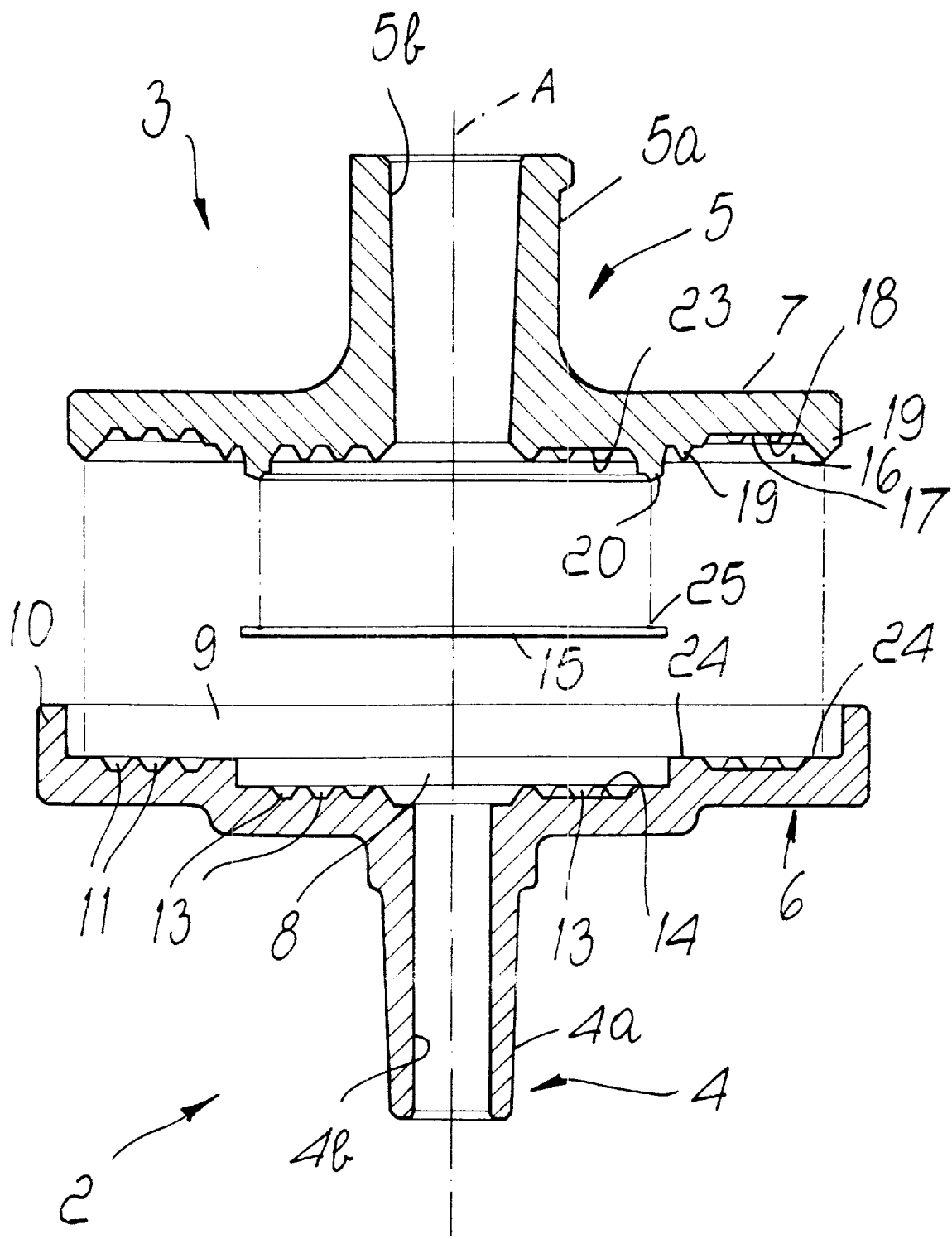
FIG. 2 is a sectional view, taken along a plane which contains the longitudinal axis during preassembly.
Figure 3:
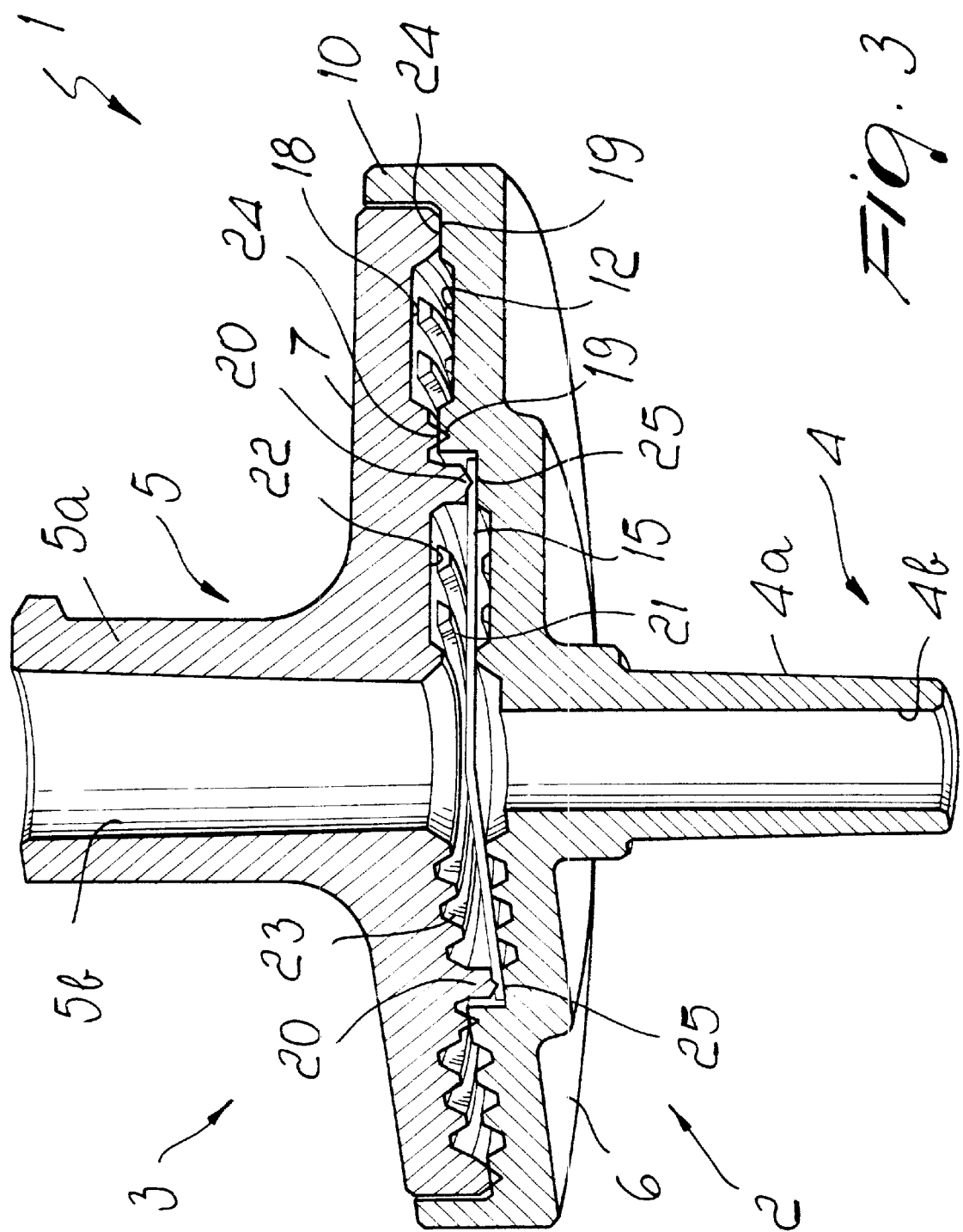
FIG. 3 is a sectional view, taken along a plane which contains the longitudinal axis, in which the flanges are coupled.

With reference to the above figures, 1 generally designates a transducer protection device particularly for hemodialysis processes according to the invention.

The device 1 comprises a first element 2 and a second element 3 which are coupled coaxially with respect to a common axis A.

Each one of the two elements 2 and 3 has a first tubular connector 4 and a second tubular connector 5, respectively, which are coaxial to the common axis A and blend with respective flanges 6 and 7.

The first connector 4 is externally provided with a frustum-shaped surface 4a inside which a cylindrical channel 4b is provided. The cylindrical channel 4b is connected to a lead, not shown in the accompanying drawings, by interlock coupling with said first connector 4. Finally, the lead leads to a pressure gauge at one of its ends.

The second tubular connector 5 is externally provided with a cylindrical surface 5a inside which there is a duct 5b having a conical cross-section and receiving a hose by interlock coupling, not shown in the accompanying drawings, which arrives from a main hose which conveys the blood to the hemodialysis machine.

The first flange 6 is frontally provided with a circular recess 8 coaxial to the common axis A. As a concentric extension of the recess 8 a flat annular seat 9 is provided from which a lip 10 rises peripherally and perimetrically encloses the seat 9. At a median region of the seat 9 there are circular grooves 11 crossed in a radial pattern by radial grooves 12 which are spaced from each other by a quarter turn.

The recess 8 has, at an annular median region, a plurality of circular channels 13 which are crossed in a radial pattern by radial channels 14 being spaced from each other by an angle of 90°. Finally, the recess 8 accommodates a circular membrane 15 whose laying and fixing methods are specified hereafter.

The second flange 7 is frontally provided with an annular cavity 16 which is coaxial to the common axis A and on which there are further circular grooves 17 which are crossed in a radial pattern by other radial grooves 18 being spaced from each other by a quarter turn. The annular cavity 16 is enclosed by edges 19 whose cross-section, along a longitudinal plane containing the common axis A, is pointed.

Continuing radially toward the center, there is a circular ridge 20 which forms a circular cylindrical cavity 21 which is coaxial to the common axis A. At the bottom 21a there is another plurality of circular channels 22 crossed radially by other radial channels 23 being spaced from each other by 90°.

After the arrangement of the membrane 15 in the recess 8, the second flange 7 is keyed in the seat 9 so that the ridge 20 rests on the border region 25 and the edges 19 rest on contacts 24.

The sealing of the two flanges 6 and 7 and the fixing of the membrane 15 between said flanges are achieved by ultrasonic thermal bonding, acting respectively at the contacts 24 and at the border region 25.

Thermal bonding at the border region 25 causes the membrane 15 to be imbibed by the melted plastics, thus providing an intimate bonding between the flanges and the membrane.

The thermal bonding performed at the contacts 24 causes, in this case also, the plastics to melt and therefore causes an intimate mutual coupling of the two flanges, so as to reinforce the seal of the membrane between said two flanges.

In practical operation, the blood arrives, through the second connector 5, at the cylindrical cavity 21 and diffuses therein through the other plurality of circular channels 22 and radial channels 23, so as to facilitate uniform distribution of the pressure applied to the membrane 15, which in addition to acting as a pressure measurement transducer is made of a semipermeable material which prevents the passage of virus-infected particles to the pressure gauge.

It has thus been shown that the invention achieves the proposed aim and objects.

In particular, the fact is stressed that the imbibition of the melted plastics by the membrane allows intimate bonding between the flanges and the membrane, so that a better seal is achieved.

Furthermore, imbibition allows to limit the risks of membrane damage.

The invention thus conceived is susceptible of numerous modifications and variations, all of which are within the scope of the inventive concept.

Figure 4:
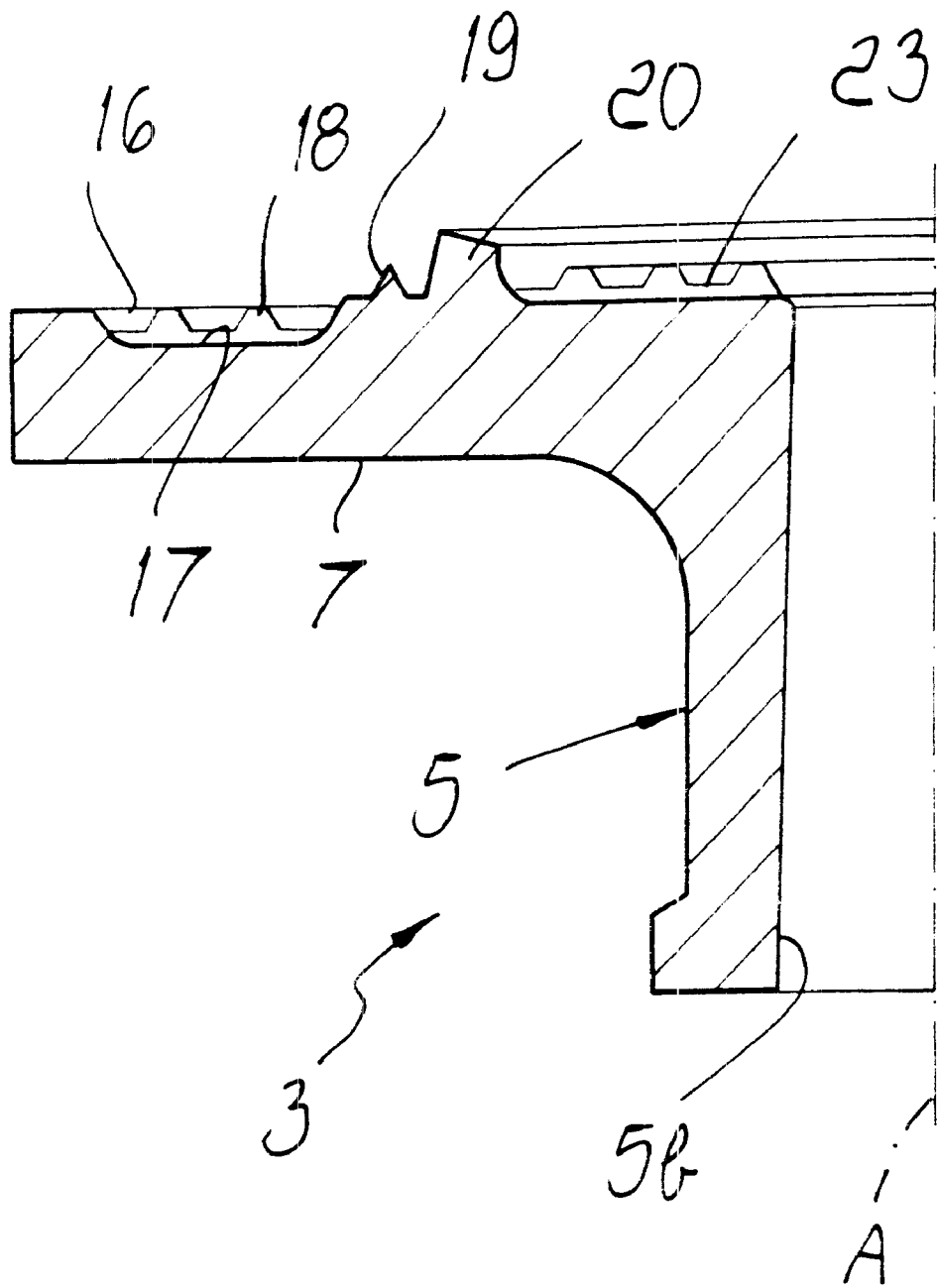
FIG. 4 is a view of another embodiment of the circular ridge that protrudes from the second flange.

Conveniently, as shown in FIG. 4, on the second flange 7 there is another embodiment of the circular ridge 20 which has a triangular cross-section whose height increases from the inner peripheral region toward the outer peripheral region of the annular ridge 20.

Moreover all the details may be replaced with other technically equivalent ones.

In practice, the materials used, as well as the shapes and the dimensions, may be any according to requirements without thereby abandoning the protective scope of the appended claims.

The disclosures in Italian Patent Application No. BO99A000602 from which this application claims priority are incorporated herein by reference.

What is claimed is:

1. A transducer protection device, particularly for hemodialysis processes, comprising: a first element; a second element said first and second elements being made of plastics and being coupled coaxially with respect to a common axis thereof; a first tubular connector; a second tubular connector; said first and second tubular connectors being each blended with a respective flange coaxial to said common axis so as to form said first and second elements, and said flanges being coupled to each other along a peripheral region thereof by ultrasonic thermal bonding; a recess formed frontally, coaxial to said common axis, on a first one of said flanges; a semipermeable membrane accommodated in said recess, in a fixed arrangement, by imbibition of melted plastics along a circular border region of said membrane upon thermal bonding; and a circular ridge which is shaped complementarily to said border region and protrudes frontally from a second one of said flanges, the thermal bonding being performed on said ridge so as to achieve intimate bonding between said first and second flanges and said membrane, further comprising an annular cavity located frontally and peripherally to said second flange, and which is coaxial to said common axis and edges having a pointed longitudinal cross-section for enclosing said annular cavity.

2. The device of claim 1, comprising an annular seat provided as a concentric extension of said recess; and a lip for peripherally enclosing said annular seat.

3. The device of claim 2, wherein said seat is formed so as to complementarily receive said second flange.

4. The device of claim 1, wherein said second flange is frontally and centrally provided with a cylindrical cavity which is coaxial to said common axis and is enclosed by said ridge.

5. The device of claim 4, further comprising, at a bottom part of said cylindrical cavity, a plurality of circular channels which are coaxial to said common axis, and a plurality of radial channels which are spaced from each other substantially by a quarter turn.

6. The device of claim 5, wherein said channels facilitate diffusion of blood in said cylindrical cavity and uniform distribution of blood pressure on said membrane.

7. The device of claim 6, wherein said ridge is provided with an edge having a triangular cross-section.

8. The device of claim 4, further comprising, at a bottom part of said recess, a plurality of circular channels which are coaxial to said common axis, and a plurality of radial channels which are spaced from each other, substantially by a quarter turn.

9. A transducer protection device, particularly for hemodialysis processes, comprising: a first element; a second element said first and second elements being made of plastics and being coupled coaxially with respect to a common axis thereof; a first tubular connector; a second tubular connector; said first and second tubular connectors being each blended with a respective flange coaxial to said common axis so as to form said first and second elements, and said flanges being coupled to each other along a peripheral region thereof by ultrasonic thermal bonding; a recess formed frontally, coaxial to said common axis, on a first one of said flanges; a semipermeable membrane accommodated in said recess, in a fixed arrangement, by imbibition of melted plastics along a circular border region of said membrane upon thermal bonding; and a circular ridge which is shaped complementarily to said border region and protrudes frontally from a second one of said flanges, the thermal bonding being performed on said ridge so as to achieve intimate bonding between said first and second flanges and said membrane, further comprising an annular cavity located frontally and peripherally to said second range, and which is coaxial to said common axis and edges having a pointed longitudinal cross-section for enclosing said annular cavity, said edges being designed to intimately bond with said first flange by ultrasonic thermal bonding in order to seal said first and second flanges thus coupled.

* * * * *